United States Patent [19]
Pelosi, Jr.

[11] 3,993,657
[45] Nov. 23, 1976

[54] [5-(4-NITROPHENYL)-2-FUROYLMETHYL]PYRIDINIUM BROMIDE

[75] Inventor: Stanford S. Pelosi, Jr., Norwich, N.Y.

[73] Assignee: Morton-Norwich Products, Inc., Norwich, N.Y.

[22] Filed: June 16, 1975

[21] Appl. No.: 586,872

[52] U.S. Cl. .............................. 260/297 R; 424/263
[51] Int. Cl.$^2$ ........................................ C07D 405/08
[58] Field of Search ................................ 260/297 R

[56] References Cited
UNITED STATES PATENTS
3,684,802   8/1972   McFarland .................... 260/297 R

OTHER PUBLICATIONS

Oleinik et al., "Chem. Abstracts" vol. 81, No. 63554b, (5–1974).

Klingsberg "Pyridine and Its Derivatives" Part two (1961) pp. 2 and 3.

Primary Examiner—Henry R. Jiles
Assistant Examiner—R. W. Ramsuer
Attorney, Agent, or Firm—Anthony J. Franze

[57] ABSTRACT

[5-(4-nitrophenyl)-2-furoylmethyl]pyridinium bromide is useful as an anti-inflammatory agent.

1 Claim, No Drawings

[5-(4-NITROPHENYL)-2-FUROYLMETHYL]-PYRIDINIUM BROMIDE

This invention is concerned with a chemical compound, namely [5-(4-nitrophenyl)-2-furoylmethyl]-pyridinium bromide of the formula:

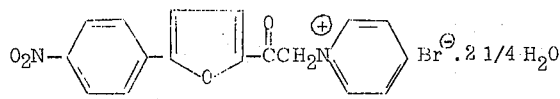

This compound possesses pharmacologic activity and is useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. (14:544 (1964)].

The method which is currently preferred for the preparation of the compound of this invention is as follows:

[5-(p-Nitrophenyl)-2-furoylmethyl]pyridinium Bromide Hydrate

A solution of 38 g (0.24 mole) of bromine in 100 ml of CCl$_4$ was added dropwise over 50 min to a stirred, refluxing mixture of 55 g (0.24 mole) of methyl 5-(p-nitrophenyl)-2-furyl ketone and 1200 ml of CCl$_4$. After the addition was complete, the reaction mixture was heated under reflux for 3/4 hr and allowed to stand at room temperature overnight. The yellow solid was collected by filtration to give 69 g (93%) of bromomethyl 5-(p-nitrophenyl)-2-furyl ketone, m.p. 153°–162°.

A mixture of 3.1 g (0.01 mole) of bromomethyl 5-(p-nitrophenyl)-2-furyl ketone, 1.0 g (0.013 mole) of pyridine and 100 ml of absolute EtOH was heated under reflux for 4 hours and cooled in ice. The solid was collected by filtration and washed with anhydrous ether to give 3.4 g (87%) of product. Recrystallization from absolute EtOH with Darco gave 3.0 g of an analytical sample, m.p. 229°–232° (dec.).

Anal. Calcd. for C$_{17}$H$_{13}$BrN$_2$O$_4$.2 1/4 H$_2$O: C, 47.51; H, 4.10; N, 6.52; H$_2$O, 9.4, Found: C, 47.49; H, 3.89; N, 6.56; H$_2$O, 9.77, 9.63.

What is claimed is:
1. A compound of the formula:

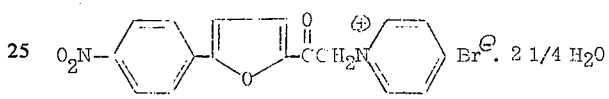

* * * * *